United States Patent
Katsuki et al.

(10) Patent No.: US 6,274,573 B1
(45) Date of Patent: Aug. 14, 2001

(54) METHOD OF TREATMENT FOR UTERINE LEIOMYOMA

(75) Inventors: Yukio Katsuki; Minoru Shimora, both of Tokyo (JP)

(73) Assignee: Mochida Pharmaceutical Co., Ltd., Tokyo (JP)

(*) Notice: Subject to any disclaimer, the term of this patent is extended or adjusted under 35 U.S.C. 154(b) by 0 days.

(21) Appl. No.: 09/529,640

(22) PCT Filed: Oct. 16, 1998

(86) PCT No.: PCT/JP98/04691

§ 371 Date: Apr. 17, 2000

§ 102(e) Date: Apr. 17, 2000

(87) PCT Pub. No.: WO99/20647

PCT Pub. Date: Apr. 29, 1999

(30) Foreign Application Priority Data

Oct. 17, 1997 (JP) .................................... 9-285826

(51) Int. Cl.$^7$ .................... A61K 31/56; A61K 38/00
(52) U.S. Cl. ................................. 514/179; 514/15
(58) Field of Search ...................... 514/179, 317, 514/329, 258, 256, 301, 15

(56) References Cited

U.S. PATENT DOCUMENTS

| | | | |
|---|---|---|---|
| 5,468,741 | 11/1995 | Yen | 514/179 |
| 5,595,756 | * 1/1997 | Bally et al. | 424/450 |
| 5,652,231 | * 7/1997 | Shibutani et al. | 514/179 |
| 6,015,789 | * 1/2000 | Suzuki et al. | 514/15 |

FOREIGN PATENT DOCUMENTS

| | | |
|---|---|---|
| 61-212596 | 9/1986 | (JP) . |
| 63-72627 | 4/1988 | (JP) . |
| 7188026 | 7/1995 | (JP) . |
| 9508418 | 8/1997 | (JP) . |

OTHER PUBLICATIONS

Shubert et al, "Natural Products Chemistry" 1984, Elsevier Science Publishers eds., 1985, pp. 143–158.
Katsuki et al, "Cancer" vol. 79, pp. 169–176, 1997.
Kawaguchi et al, "American Journal of Obstetrics and Gynecology" vol. 160, pp. 637–641, 1988.
Carr et al, "Journal of Clinical Endocrinology Metabolism" vol. 76, pp 1217–1223, 1993.
Rein et al, "American Journal of Obstetrics & Gynecology" vol. 172, pp. 14–18, 1995.
Murphy et al, Journal of Clinical Endocrinology, vol. 76, pp. 513–517, 1993.
Aoki et al, Obstetrics & Gynecology, vol. 83, pp. 220–228, 1994.
Sasakawa et al, "Japanese Journal of Pharmacology" Suppl. vol. 67, p. 162, 1995.
Friedman et al, "Fertility and Sterility", vol. 49, pp. 404–409, 1988.
Kawaguchi et al. "Am. J. Obstet Gynecol.", vol. 160, No. 5, pp. 637–641, (1989).
Carr et al. "J. of Clinical Endocrinology and Metabolism", vol. 76, No. 5, pp. 1217–1223, (1993).
Kohler et al., "Archives of Gynecology and Obstetrics", vol. 254, pp. 594–595 (1993). Intro & Summary only.

* cited by examiner

*Primary Examiner*—Jon P. Weber
*Assistant Examiner*—Patricia D Patten
(74) *Attorney, Agent, or Firm*—Birch, Stewart, Kolasch & Birch, LLP

(57) ABSTRACT

Providing a therapeutic agent of uterine leiomyoma, containing dienogest and a solvate thereof as the effective ingredient with less adverse effects, which can be used either singly or in combination with GnRH and can be administered or pharmaceutically manufactured as oral, transdermal dosing agents or suppositories.

11 Claims, 1 Drawing Sheet

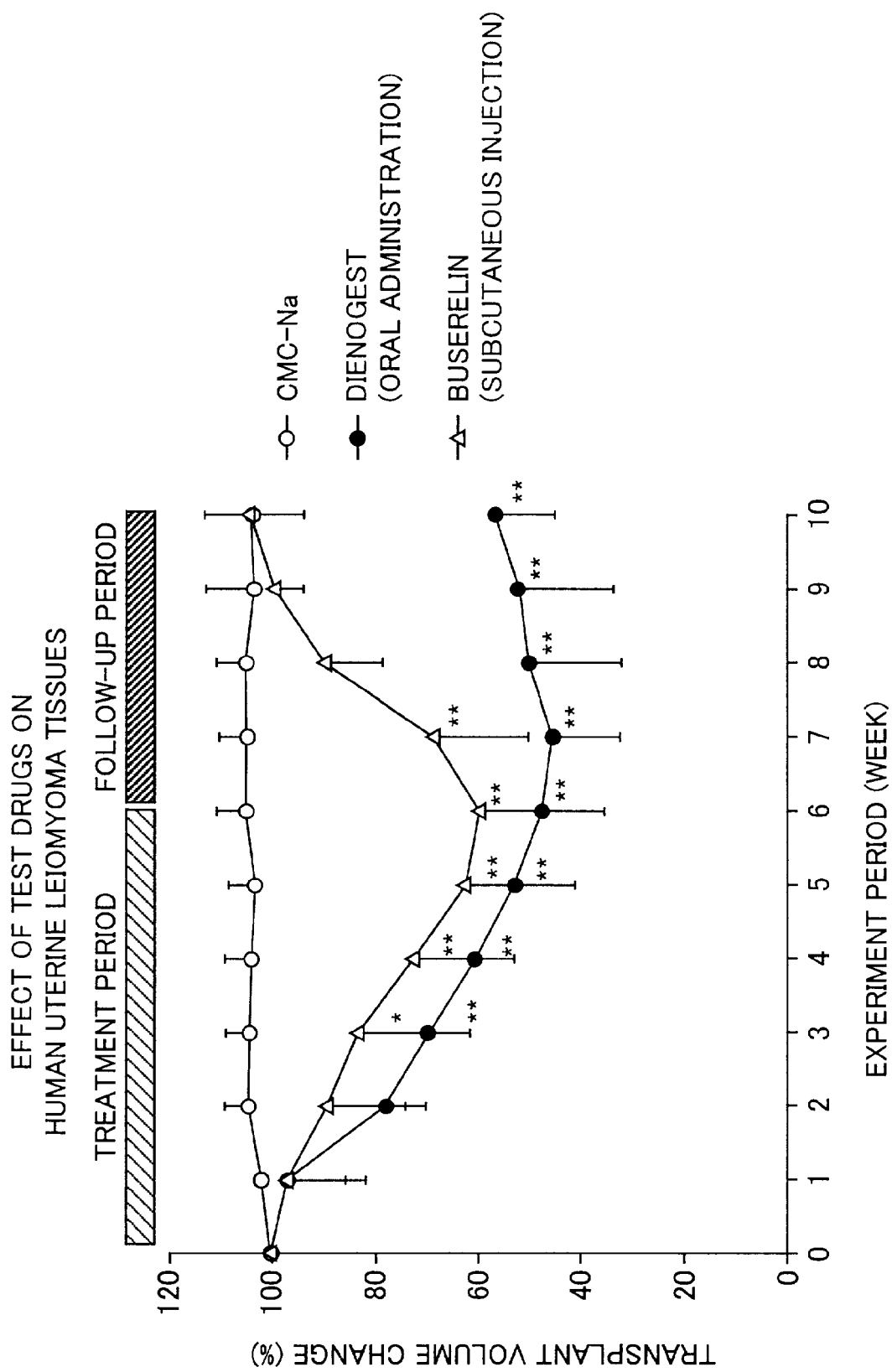

METHOD OF TREATMENT FOR UTERINE LEIOMYOMA

This application is the national phase under 35 U.S.C. §371 of PCT International Application No. PCT/JP98/04691 which has an International filing date of Oct. 16, 1998, which designated the United States of America.

TECHNICAL FIELD

The present invention relates to a therapeutic agent of uterine leiomyoma, having less adverse effects such as the reduction of bone density, wherein the agent can be used singly or can be used in combination with GnRH agonists and wherein the agent can be administered for a long term.

BACKGROUND ART

Dienogest is the International Nonproprietary Name (INN) of a known compound with the following structure (17 α-cyanomethyl-17β-hydroxy-estra-4, 9(10) -dien-3-one) represented by the following formula (1).

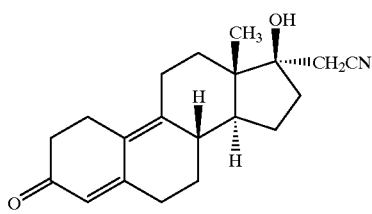

(I)

The properties of the compound and a method for synthesizing the compound are generally described by Shubert, et al., Natural Products Chemistry 1984, Elsevier Science Publishers eds., 1985, pp.143–158.

Dienogest has been known to have progestational activity. In Germany, a combined drug of dienogest with ethinylestradiol has been introduced as an oral contraceptive into market. Additionally, the clinical development of dienogest as a therapeutic agent of endometriosis is ongoing (Kohler et al., Archives of Gynecology and Obstetrics, Vol.254, pp.594–595, 1993), and experimental reports have been issued to demonstrate the carcinostatic action of dienogest on uterine cancer and breast cancer (Katsuki et al., Japanese Patent Laid-open No. Hei 7–188026; Katsuki, et al., Cancer, Vol.79, pp.169–176, 1997). However, no report has been published yet to indicate the therapeutic effectivity of dienogest on uterine leiomyoma.

It is said that uterine leiomyoma is present in 20 to 40% of females above 30 years old, and uterine leiomyoma is one of diseases found the most frequently in the field of obstetrics and gynecology. Uterine leiomyoma is clearly different from endometriosis and uterine cancer in view of that uterine leiomyoma is a benign tumor of smooth muscle. Uterine leiomyoma develops mainly during reproductive ages and stops its growth or reduces its tumor size after menopause or castration. And, a hormone therapy with gonadotropin releasing hormone (GnRH) agonists typically including buserelin acetate has been indicated widely to treat uterine leiomyoma.

Although GnRH agonists have therapeutic effects on uterine leiomyoma, the decrease of bone minerals as well as adverse effects such as climacteric disorders occur at a high frequency, because of the reduction of blood estrogen level due to the main action mechanism of the agents. Because of these risks, the period of dosing GnRH agonists is generally limited not to exceed 6 months.

Moreover, a rebound phenomenon has been known that the uterine leiomyoma will restore the size before the therapy if the administration of GnRH agonists is discontinued (Freidman et al., Fertility and Sterility, Vol.49, pp.404–409, 1988).

In order to treat concomitant symptoms of uterine leiomyoma, an attempt was made in the past to use progestins typically including medroxyprogesterone acetate. However, the ability of progestins when administered singly for the treatment of uterine leiomyoma is now doubtful. When a progestin agent was administered to a patient with uterine leiomyoma, for example, the increase in number of mitotic cells in uterine leiomyoma tissues was observed (Kawaguchi et al., American Journal of Obstetrics and Gynecology, Vol.160, pp.637–641, 1988; Fujii et al., Molecule & Cell Biology, pp.46–57, 1997). It is suggested that progesterone has an critical role in the pathogenesis of uterine leiomyoma, on the basis of the findings that oral contraceptives cause the increase in the size of uterine leiomyoma and that uterine leiomyoma increases its size during pregnancy, i.e., a state of a high progesterone level in blood.

For the purpose of preventing the adverse effects of GnRH agonists as described above, a number of sex hormonal agents have been tried and used in combination. However, estrogenic agents are not appropriate because of their risks due to the direct stimulating action on leiomyoma tissues. In addition, there are number of reports showing that the attempts to use a GnRH agonist plus medroxyprogesterone (MPA) in combination were effective to reduce the adverse effects of the GnRH agonist such as hot flush and bone mineral loss, but that such trials often resulted in the enlargement of the size of leiomyoma lesion in compared to that of the treatment with the GnRH agonist alone. In other words, it is said that progestins contradict the therapeutic effect of GnRH agonists on uterine leiomyoma (Freidman et al., supra.; Carr et al., Journal of Clinical Endocrinology Metabolism, Vol.76, pp.1217–1223, 1993; Rein et al., American Journal of Obstetrics and Gynecology, Vol.172, pp.14–18, 1995).

Furthermore, it has been reported that the administration of RU-486, an anti-progestin could reduce the volume of uterine leiomyoma and the agent was therefore effective (Murphy et al., Journal of Clinical Endocrinology, Vol.76, pp.513–517, 1993; Yen et al., U.S. Pat. No. 5,468,741), so that the development of a therapeutic agent of uterine leiomyoma on the concept of anti-progestin is now under way (Murphy et al., supra; Hodogen et al., Published Japanese translation of PCT international publication for patent application No. Hei 9–508418). In recent years, accordingly, it is believed that progestins serve as a growth promoting factor for uterine leiomyoma (Rein et al., supra; Fujii et al., supra) and that the agents work adversely in the medical treatment of uterine leiomyoma. In these circumstances, dienogest has not been applied to treat uterine leiomyoma.

DISCLOSURE OF THE INVENTION

As has been described above, GnRH agonists are widely used currently for the treatment of uterine leiomyoma, but because of higher frequencies of the occurrence of adverse effects such as bone resorption action or climacteric disorders, the dosing period of the agonists is limited. Additionally, the rebound phenomenon after the stopping of the dosing is a serious problem. Hence, the development of a therapeutic agent with no such adverse effect or no such problem is demanded. Furthermore, the development of a novel pharmaceutical agent has also been desired, which never eliminates the therapeutic effect of GnRH agonists on uterine leiomyoma even if used as an agent in combination with GnRH agonists or never cause a regrowth of the uterine leiomyoma after the treatment with the GnRH agonists and at least reduces the adverse effects of the GnRH agonists. The present invention can overcome at least one of these problems.

In the circumstances mentioned above, the present inventors have made investigations to search an agent effective for uterine leiomyoma and simultaneously with less adverse effects or problems of the GnRH agonists. Quite unexpectedly, the inventors have found that dienogest has an ability to fulfill those requirements.

Dienogest has an action to reduce the volume of human uterine leiomyoma tissues. Still further, dienogest generally never affects the level of bone minerals, unlike GnRH agonists and the rebound phenomenon after the stopping of the dosing is remarkably prohibited. Based on these findings, the inventors have continued their investigations. Consequently, the invention has been achieved.

Dienogest as the effective ingredient of the therapeutic agent of uterine leiomyoma in accordance with the present invention is a compound with a structure represented by the formula (I) as described above and can form a solvate with various solvents pharmaceutically acceptable, such as water, ethanol, glycerol and acetic acid.

A first aspect of the present invention is a therapeutic agent of uterine leiomyoma, containing dienogest or a solvate thereof as the effective ingredient. Furthermore, it is a therapeutic agent of uterine leiomyoma that contains dienogest or a solvate thereof as the effective ingredient and by which the rebound phenomenon after the stopping of the dosing is prohibited.

A second aspect of the present invention is a therapeutic agent of uterine leiomyoma, for use in combination with other therapeutic agents of uterine leiomyoma. Other therapeutic agents in combination with the therapeutic agent of uterine leiomyoma are preferably GnRH agonists, GnRH antagonists, aromatase inhibitors and antiestrogens.

A third aspect of the present invention is the therapeutic agent of uterine leiomyoma after discontinuation of GnRH agonists and GnRH antagonists.

The present invention concurrently provides a method for therapeutically treating uterine leiomyoma by using dienogest or a solvate thereof; a method for producing a therapeutic agent of uterine leiomyoma, wherein the agent contains dienogest or a solvate thereof; and a use of dienogest or a solvate thereof for producing a pharmaceutical composition for prevention and/or treatment of uterine leiomyoma.

The therapeutic agent of the present invention as described above may be used for preventing uterine leiomyoma and preventing the recurrence of uterine leiomyoma.

BRIEF DESCRIPTION OF THE DRAWINGS

FIG. 1 shows the results of statistical total analysis of the action that the test drugs influences the human uterine leiomyoma tissues using 4 transplantation samples of donors.

BEST MODE FOR CARRYING OUT THE INVENTION

The effects of the therapeutic agent of uterine leiomyoma in accordance with the present invention will now more specifically be described in the following experimental examples. Among pharmaceutical agents used for comparison, buserelin acetate is a typical GnRH agonist formulation, and is indicated for uterine leiomyoma. Additionally, MPA is the most typical progestin and can be orally given, like dienogest.

Experimental Example 1

Action of Reducing Human Uterine Leiomyoma Tissues

Uterine leiomyoma tissues isolated from a patient with uterine leiomyoma by hysterectomy were used. According to the method by Aoki et al. (Obstetrics and Gynecology, Vol.83, pp.220–228, 1994), uterine leiomyoma tissues were cut into pieces of 2-mm cube and were then transplanted subcutaneously into the dorsal region of female CB-17 SCID-strain mice ranging 17 to 21 g of body weight, at one piece per one mouse. Three weeks after the transplantation, the viable transplant was confirmed. Thereafter, these mice were grouped per one group of two mice. A first group was given the solvent (0.5% carboxymethyl cellulose solution; abbreviated as "CMC" hereinbelow), which was defined as control group. Continuously for 6 weeks, dienogest and MPA dissolved or suspended in CMC were administrated orally, while buserelin acetate was administered subcutaneously.

Prior to or after the treatment with the drugs for 6 weeks, the volumes of the uterine leiomyoma transplants were measured by ultrasonography (type SSD-650, manufactured by Aloka, Tokyo) according to the method by Aoki et al., and the volume change (%) of the uterine leiomyoma transplant in each animal was calculated by the following calculation formula (A);

$$\text{volume change } (\%) = \frac{[X] - [Y]}{[Y]} \times 100 \qquad (A)$$

wherein
X is a volume of each group after treatment;
Y is a volume of each group prior to treatment.
The results are shown in Table 1.

TABLE 1

Effect of test drugs on human uterine leiomyoma tissues

| Group | Dose (mg/kg/day) | Volume change (%) |
|---|---|---|
| Control | — | +12.5 |
| Dienogest | 0.1 | −56.0 |
|  | 1 | −63.0 |
| MPA | 1 | +116.7 |
| Buserelin acetate | 0.03 | −41.9 |

The numerical figures in the table are mean values of two mice in each group.

The results in Table 1 show that a significant reducing action was observed in the groups given with dienogest at doses of 0.1 and 1 mg/kg and the group given with buserelin acetate at a dose of 0.03 mg/kg, while the volume of the transplant slightly increased in the control group after the dosing period, compared to that of the before. The dose of buserelin acetate used was a sufficient dose enough for gonadotropin to be lowered in animals and is a dose with sufficient efficacy if calculated on a clinical dose base. Quite surprisingly, the reducing action of dienogest exceeds the action of buserelin acetate, involving higher efficacy. In the MPA dosed group, alternatively, the volume of the transplant was prominently increased.

Experimental Example 2

Actions of Reducing Human Uterine Leiomyoma Tissues and Prohibiting Rebound Phenomenon Uterine leiomyoma tissues isolated from four patients (donors) with uterine leiomyoma by hysterectomy were used. According to the procedure of Experimental Example 1, leiomyoma tissues of 2-mm cube were transplanted subcutaneously to female SCID-strain mice. Three weeks after the transplantation, it was confirmed that all the transplants were viable. Thereafter, these mice were grouped per group of two mice for each donor. A first group was given CMC, which was defined as control group. Continuously for 6 weeks (treatment period), dienogest suspended in CMC was administered orally, while buserelin acetate was administered subcutaneously. Every group was observed for successive 4 weeks after the end of the administration of the drugs (follow-up period). During the experiment period, the volumes of the transplants were measured once a week according to the procedure of Experimental Example 1. The volume of the transplant prior to the administration of the drug in each animal was taken as 100%, and the ratios of the former to the latter were calculated. The average of the values obtained from two mice of the same group for the same donor was shown as a result example. During the whole experiment period, the size change of each transplant was measured every week, and the transplants of four donors were totally analyzed. The result of each group was shown as the average +/− standard deviation (n=4), and the differences between the values of each group and control group were analyzed by Dunnett's test (★$P<0.05$, ★★$P<0.01$). The analysis results are shown in FIG. 1 as the evolution of the transplant volume changes in the treatment period and the follow-up period.

Further, the transplant volume changes prior to and after the follow-up period are summarized for each donor in Table 2.

such change was remarkably prohibited in the groups of dienogest administration.

As to the toxicity (safety) of the therapeutic agent of uterine leiomyoma in accordance with the present invention, the effective dose of dienogest on uterine leiomyoma tissues as demonstrated in the present Experimental Example is a dose almost equal to the clinical dose (2 mg/day) of the drug which has been already used as an oral contraceptive in Germany and the safety has been verified at clinical trials using this drug alone (at a dose of 1 to 4 mg per body per day) as a therapeutic agent of uterine leiomyoma. It is thus believed that no problem occurs.

The experimental results mentioned insofar demonstrate that dienogest prominently reduces the transplanted uterine leiomyoma and can be used as a therapeutic agent of uterine leiomyoma, apparently unlike conventional progestins, while MPA works as a growth factor of uterine leiomyoma and is therefore inappropriate as the therapeutic agent. Furthermore, it is considered that the efficacy of dienogest exceeds that of the preexisting agents for uterine leiomyoma (GnRH agonists) and that dienogest may be a candidate of a new therapeutic agent of uterine leiomyoma.

Because dienogest generally never affects the level of bone minerals, unlike GnRH agonists (Sasakawa et al., Japanese Journal of Pharmacology, Suppl. Vol.67, p.162, 1995), furthermore, dienogest may possibly serve as a therapeutic agent of uterine leiomyoma with less adverse effects.

The therapeutic agent of uterine leiomyoma in accordance with the present invention can be used in various aspects of hormone therapy. More specifically, the agent is administered singly for uterine leiomyoma. Additionally, the dosage thereof in combination with preexisting agents for hormone therapy for the purpose of treating uterine leiomyoma is also considered. The combination dosage includes simple simultaneous administration with GnRH agonists to patients, and may additionally include add-back therapy, and the use thereof during discontinuation period of GnRH agonists. In

TABLE 2

Effect of test drugs on human uterine leiomyoma tissues
(comparison between treatment period and follow-up period)

| | Volume change of leiomyoma (%) | | | | | | | |
|---|---|---|---|---|---|---|---|---|
| | Transplant (donor A) | | Transplant (donor B) | | Transplant (donor C) | | Transplant (donor D) | |
| Drug dose (mg/kg/day) | After treatment | After follow-up | After treatment | After follow-up | After treatment | After follow-up | After treatment | After follow-up |
| Control (−) | 0.0 | −7.1 | +8.3 | +11.7 | 0.0 | 0.0 | +10.0 | +10.0 |
| Dienogest (0.1) | −57.9 | −56.2 | −43.6 | −30.5 | −68.1 | −51.2 | −41.2 | −34.5 |
| Buserelin (0.1) | −44.6 | −7.7 | −30.5 | +16.7 | −56.0 | 0.0 | −29.2 | +10.0 |

In this experiment, the effect of 0.1 mg/kg/day of dienogest on the reduction of uterine leiomyoma was superior to that of 0.1 mg/kg/day of buserelin (by subcutaneous administration).

The results in the follow-up period showed that the rebound phenomenon that the reduced leiomyoma transplant is enlarged again after the end of the administration, was confirmed in the groups of buserelin administration, whereas the add-back therapy, the single dosing period of GnRH agonists is combined with the simultaneous dosing period of the therapeutic agent, and the length of each period and the dose should be adjusted to the conditions of patients. With reference to the MPA dosage for add-back therapy disclosed in the Friedman's reference, Friedman et al. (Fertility and Sterility, Vol.49, pp.404–409, 1988) as one specific example, the present agent may satisfactorily be used.

In the add-back therapy, dienogest may be used alone. Still further, estrogen may satisfactorily be used in combination.

Dienogest has also an antagonistic action against the bone mineral loss, an adverse effect of GnRH agonists, and the agent can enhance the principal therapeutic action of GnRH agonists when used in combination but reduces the adverse effects. Therefore, GnRH agonists are preferable as a combination agent.

The dosage form of the therapeutic agent of uterine leiomyoma of the present invention is described below. The therapeutic agent of uterine leiomyoma may be administered either alone or with other drugs. Specific examples of the dosage form includes oral or parenteral forms, for example tablets, capsules, tablets coated with sugar or pharmaceutical coating materials, granules, fine granules, powders, liquid solutions or suspensions, emulsions, fatty emulsions, ointments and the like; and additionally includes intra-rectal or intra-vaginal suppositories. The agent may be injected subcutaneously, intra-muscularly and intravenously. The dosage form additionally includes sustained release formulations such as patches, tapes, and intradermal implants.

The dose is about 0.5 to 10 mg/day/adult, preferably 1 to 5 mg/day/adult, in one single dose to in 5 divided doses. Of course depending on the age, body weight and health status of a patient as well as the dosage route, the dose and dosing number may be varied.

Specific examples of pharmaceutical agents to be used in combination with the therapeutic agent of uterine leiomyoma of the present invention includes GnRH agonists such as buserelin, leuprorelin, goserelin, nafarelin, triptorelin, deslorelin, avorelin, etc.; and GnRH antagonists such as cetrorelix, ganirelix, ramorelix, and Antide and so on. Herein, the GnRH antagonists are agents for treating uterine leiomyoma directly blocking GnRH receptors and thereby exerting an action to suppress estrogen. Other hormonal agents include danazol, and antiestrogen agents such as tamoxifen and clomiphene. Aromatase inhibitors include fadrozole and vorozole and the like.

Examples of the present invention will now be described below. The present invention is not at all limited to the following examples.

EXAMPLE 1

| Dienogest | 2.0 g |
|---|---|
| Lactose | 87.0 g |
| Corn starch | 6.0 g |
| Magnesium stearate | 5.0 g |

The ingredients are mixed together, and each 100 mg of the resulting mixture is sealed in capsule No.3 according to Japanese Pharmacopoeia, to prepare capsules.

EXAMPLE 2

| Dienogest | 0.4 g |
|---|---|
| Lactose | 91.6 g |
| Corn starch | 50.0 g |
| Talc | 3.0 g |
| Magnesium stearate | 5.0 g |

The ingredients are appropriately mixed together, to prepare tablets by wet granule compaction process. Each tablet (150 mg) contains 0.40 mg of dienogest.

EXAMPLE 3

| Dienogest | 1.5 g |
|---|---|
| Polyoxyethylene lauryl ether | 38.5 g |
| Glycerin | 20.0 g |

The ingredients are appropriately melt kneaded together, and the resulting mixture is sealed in a plastic package, to prepare suppositories each of a weight of 1.0 g.

EXAMPLE 4

| Dienogest | 1.0 g |
|---|---|
| Polysolbate 80 | 1.0 g |
| Witepzol (S-55) | 98.0 g |

The ingredients are kneaded together under heating, and the resulting mixture is sealed in a plastic package, to prepare suppositories each of a weight of 1.0 g.

Industrial Applicability of the Invention

The therapeutic agent of uterine leiomyoma of the present invention is expected to exert therapeutic effects comparable or superior to the conventional agents for hormone therapy. For example, the agent is expected to exert the therapeutic effects on patients never completely treated with such conventional GnRH agonists. Furthermore, the therapeutic agent of uterine leiomyoma of the present invention has no problem of serious adverse effects of conventional hormonal agents (particularly GnRH agonists) so that the agent of the present invention can be administered safely for a long time compared with conventional agents. More specifically, the agent does not cause any occurrence of bone resorption action or climacteric symptoms, and therefore, the agent can be administered continuously for a term of 6 months or more. Additionally, the agent can be administered for a long time until menopause, to reduce the uterine leiomyoma. Furthermore, it is expected that the agent possibly causes little rebound phenomenon during a discontinuation stage of the agent. Even in the combination with GnRH agonists and the like, the agent is expected to suppress the adverse effect of GnRH agonists such as bone resorption or without reducing the therapeutic effect of GnRH agonist. The agent can be administered as a drug with higher safety during a discontinuation stage of GnRH agonists and the like.

What is claimed is:

1. A method of reducing the recurrence of uterine leiomyoma comprising administering to a patient in need thereof a pharmaceutical composition containing an effective amount of dienogest or a pharmaceutically acceptable solvate thereof as an effective component and a pharmaceutically acceptable carrier.

2. A method of treating uterine leiomyoma comprising administering to a patient in need thereof a pharmaceutical composition containing an effective amount of dienogest or a pharmaceutically acceptable solvate thereof as an effective component and a pharmaceutically acceptable carrier.

3. The method of claim 1 or 2, wherein the effective amount is about 0.5 to 10 mg/day/adult.

4. The method of claim 3, wherein the effective amount is administered in from one to five doses.

5. The method of claim 4, wherein the dosage is administered orally, parenterally, transdermally, intradermally, intra-rectally, intra-vaginally, by subcutaneous injection, by intra-muscular injection, by intravenous injection, by patches, by tapes or by intradermal implants.

6. The method of claim 4, wherein the dosage form is selected from the group consisting of tablets, capsules, tablets coated with sugar or pharmaceutical coating materials, granules, fine granules, powders, liquid solutions, liquid suspensions, emulsions, fatty emulsions, ointments intra-rectal suppositories, and intra-vaginal suppositories.

7. A method of treatment of uterine leiomyoma comprising administering to a patient in need thereof a pharmaceutical composition containing dienogest or a pharmaceutically acceptable solvate thereof in combination with agents selected from the group consisting of gonadotropin releasing hormone agonists, gonadotropin releasing hormone antagonists, antiestrogen agents and aromatase inhibitors and a pharmaceutically acceptable carrier.

8. A method of reducing the recurrence of uterine leiomyoma comprising administering to a patient in need thereof a pharmaceutical composition containing dienogest or a solvate thereof in combination with agents selected from the group consisting of gonadotropin releasing hormone agonists, gonadotropin releasing hormone antagonists, antiestrogen agents and aromatase inhibitors and a pharmaceutically acceptable carrier.

9. The method of claim 8 or 7, wherein the gonadotropin releasing hormone agonists are selected from the group consisting of buserelin, leuprorelin, goserelin, nafarelin, triptorelin, deslorelin, avorelin, cetrorelix, ganirelix, remorelix, and Antide.

10. The method of claim 8 or 7, wherein the antiestrogen agents are selected from the group consisting of tamoxifen and clomiphene.

11. The method of claim 8 or 7, wherein the aromatase inhibitors are selected from the group consisting of fadrozole and vorozole.

* * * * *